US00PP20179P2

(12) United States Plant Patent
Braasch

(10) Patent No.: US PP20,179 P2
(45) Date of Patent: Jul. 14, 2009

(54) ***BOUGAINVILLEA LIBERTATIS* PLANT NAMED 'LIBERTY FLAME'**

(50) Latin Name: *Bougainvillea libertatis*
Varietal Denomination: Liberty Flame

(76) Inventor: Hermann Braasch, 36655 N. 25th St., Cave Creek, AZ (US) 85331

( * ) Notice: Subject to any disclaimer, the term of this patent is extended or adjusted under 35 U.S.C. 154(b) by 0 days.

(21) Appl. No.: 11/652,254

(22) Filed: Jan. 11, 2007

(51) Int. Cl.
*A01H 5/00* (2006.01)

(52) U.S. Cl. ..... Plt./256
(58) Field of Classification Search ..... Plt./256
See application file for complete search history.

(56) References Cited

U.S. PATENT DOCUMENTS

| | | | |
|---|---|---|---|
| PP6,349 | P | 10/1988 | Ingwersen et al. |
| PP8,826 | P | 7/1994 | Hatten |
| PP8,827 | P | 7/1994 | Hatten |
| PP10,950 | P | 6/1999 | van Rijn |
| PP11,177 | P | 1/2000 | van Rijn |
| PP11,274 | P | 3/2000 | van Rijn |
| PP15,403 | P2 | 12/2004 | van Rijn |
| PP15,429 | P2 | 12/2004 | van Rijn |
| PP16,390 | P3 | 3/2006 | Iredell et al. |

*Primary Examiner*—June Hwu
(74) *Attorney, Agent, or Firm*—Andrew P. Lahser

(57) ABSTRACT

A new and distinct *Bougainvillea* particularly distinguished from other *Bougainvillea* plants by its variegated leaf, flowering coloration, and upright to spreading woody growth habit. The leaves have a definite and distinct variegation of light and dark green; and its leaves and bracts have an attractive flowering coloration.

6 Drawing Sheets

Latin name: Botanical classification/cultivar designation: *Bougainvillea libertatis,* a member of the Nyctaginaceae family, hereinafter referred to by the cultivar name 'Liberty Flame'.

BACKGROUND OF THE NEW PLANT

The present invention relates to a new and distinct cultivar of *Bougainvillea* plant, hereinafter referred to by the name 'Liberty Flame'.

The new *Bougainvillea* is a naturally occurring branch mutation of a *Bougainvillea* 'Torch Glow', U.S. Plant Pat. No. 6,349. The new *Bougainvillea* was discovered and selected by the inventor from within a population of plants in a controlled, residential environment in Cave Creek, Ariz. May, 2006. The selection of this plant was based on its attractive, variegated leaf, floral coloration and bushy growth habit.

Asexual reproduction of the new cultivar by cuttings in Cave Creek, Ariz. since May, 2006 has shown that the unique features of this new *Bougainvillea* are stable and reproduced true to type in successive generations.

SUMMARY OF THE NEW PLANT

Plants of the cultivar, 'Liberty Flame' have not been observed under all possible environmental conditions. Phenotypic characteristics may very somewhat with variations in environment such as temperature and or light intensity without, however, any variance in the genotype.

The variegated leaves been repeatedly observed and are determined to be one of the unique characteristics of 'Liberty Flame'.

Plants of the new *Bougainvillea* are most similar to plants of the parent, *Bougainvillea* 'Torch Glow', U.S. Plant Pat. No. 6,349. In side-by-side comparisons conducted in Cave Creek, Ariz. plants of the new *Bougainvillea* differed primarily from plants of parent selection primarily in the leaf variegation. The plants also differ in leaf structure and growth habits.

BRIEF DESCRIPTION OF THE PHOTOGRAPHS

The accompanying colored photographs illustrate the overall appearance of the new cultivar, showing the color is as true as it is reasonably possible to obtain in colored reproductions of this type. Colors in the photographs may differ from the color values cited in the detailed botanical descriptions, which accurately describes the colors of the new *Bougainvillea.*

DETAILED BOTANICAL DESCRIPTION

Figure 1:
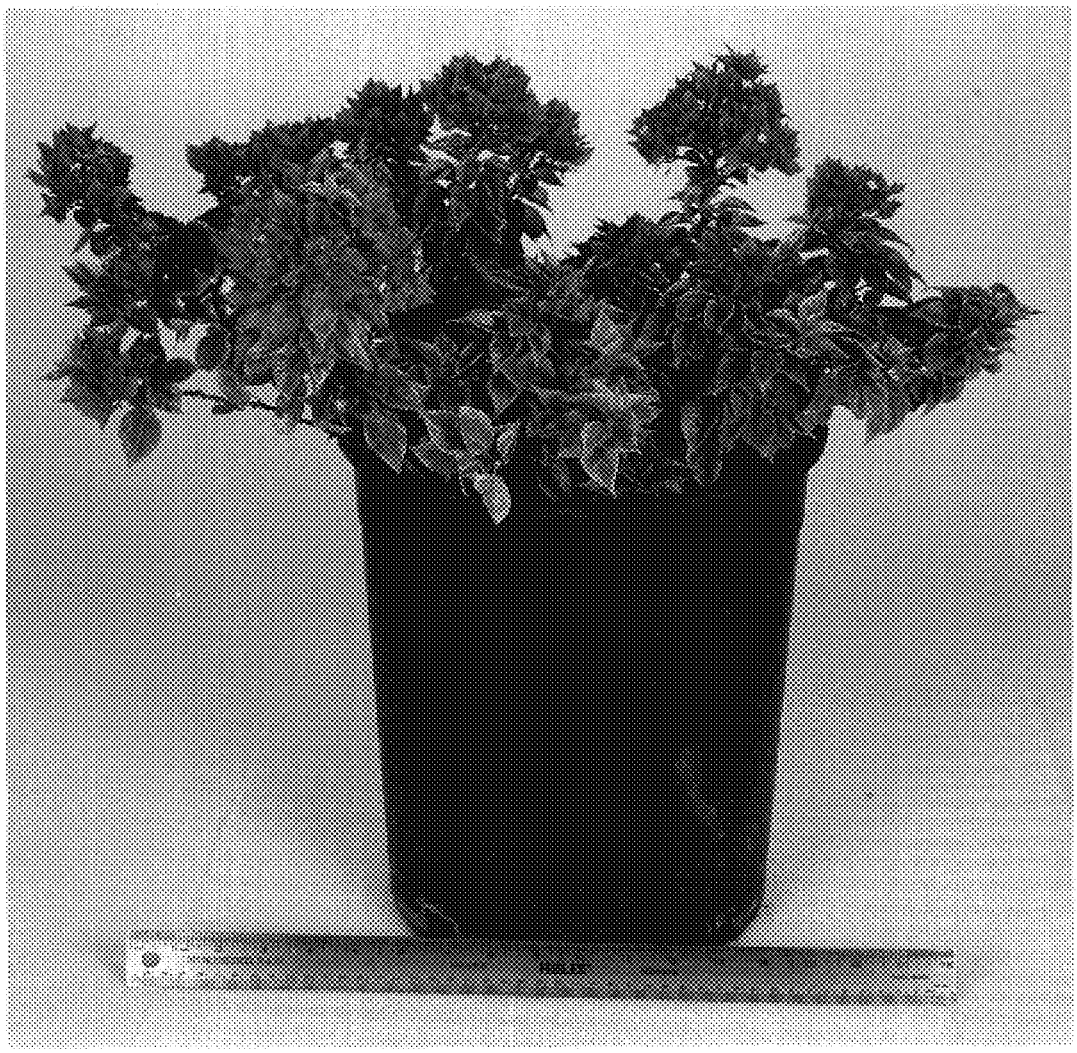
FIG. 1 shows a side perspective view illustrating a typical 6 month old plant of 'Liberty Flame' grown in containers in an outdoor nursery.
Figure 2:
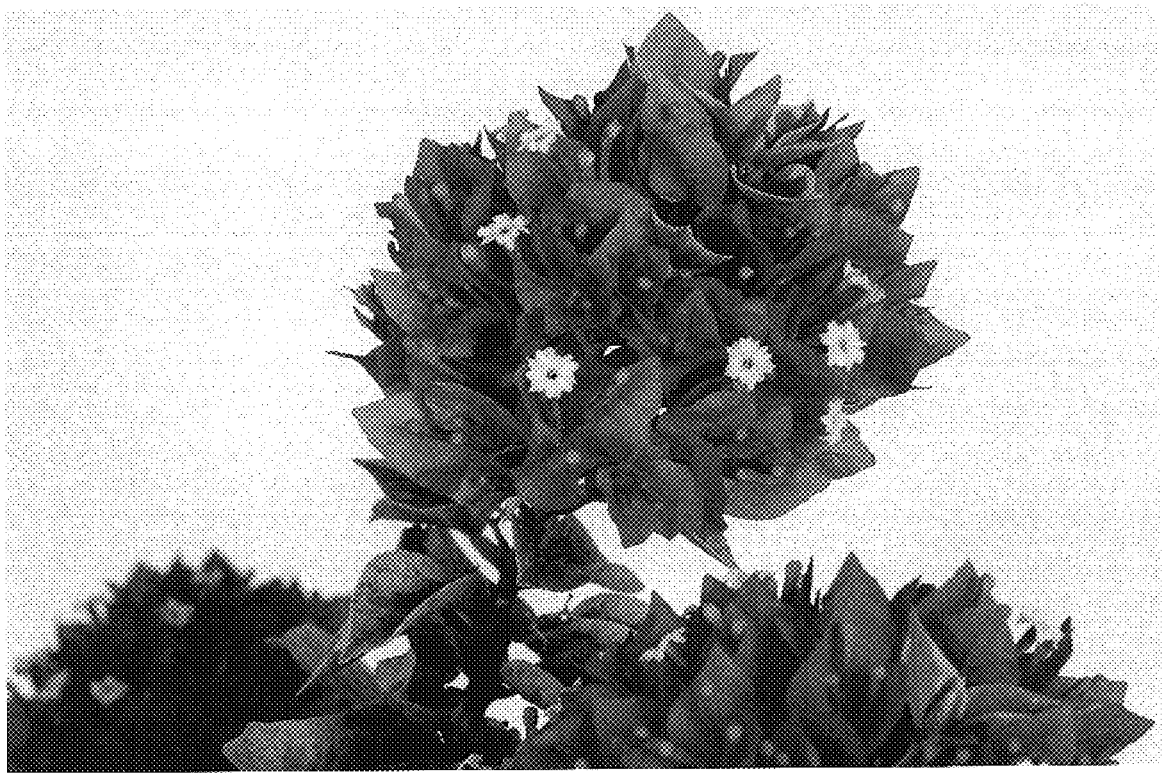
FIG. 2 shows a close-up view illustrating typical inflorescence with some leaves of 'Liberty Flame'.
Figure 3:
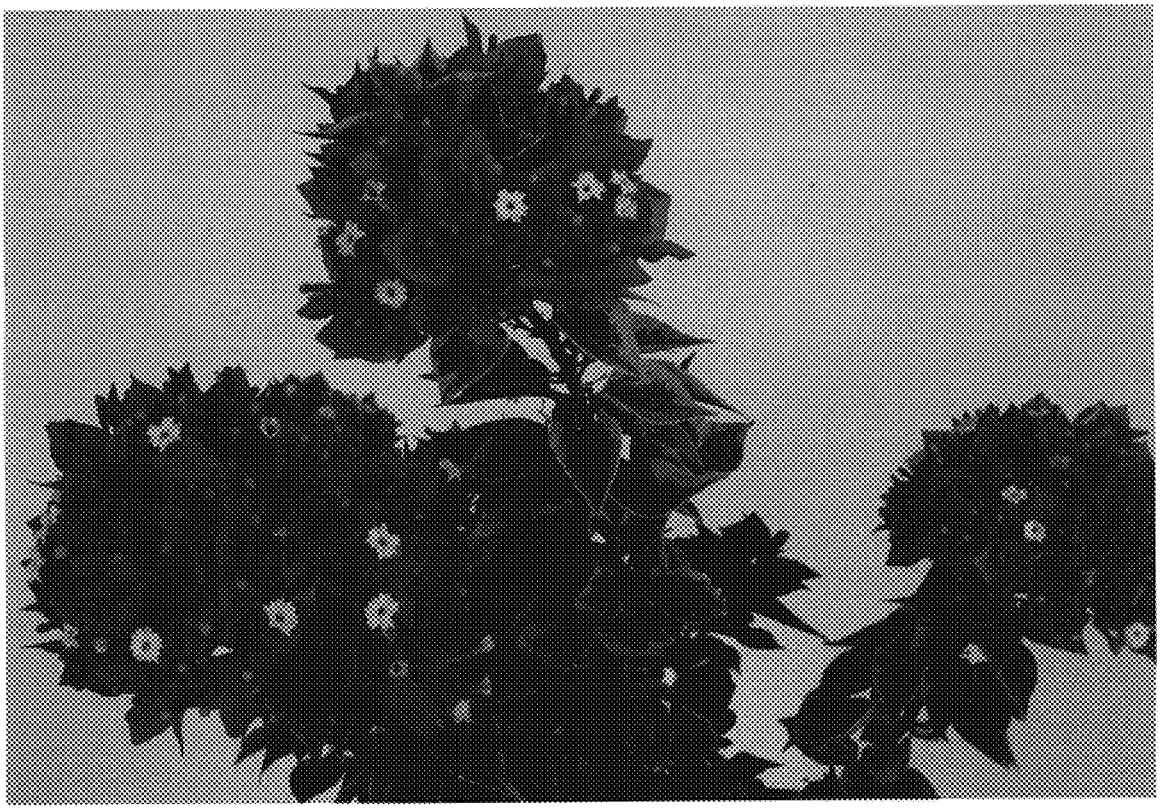
FIG. 3 shows a close-up view illustrating typical developing flowers and bracts of 'Liberty Flame'.
Figure 4:
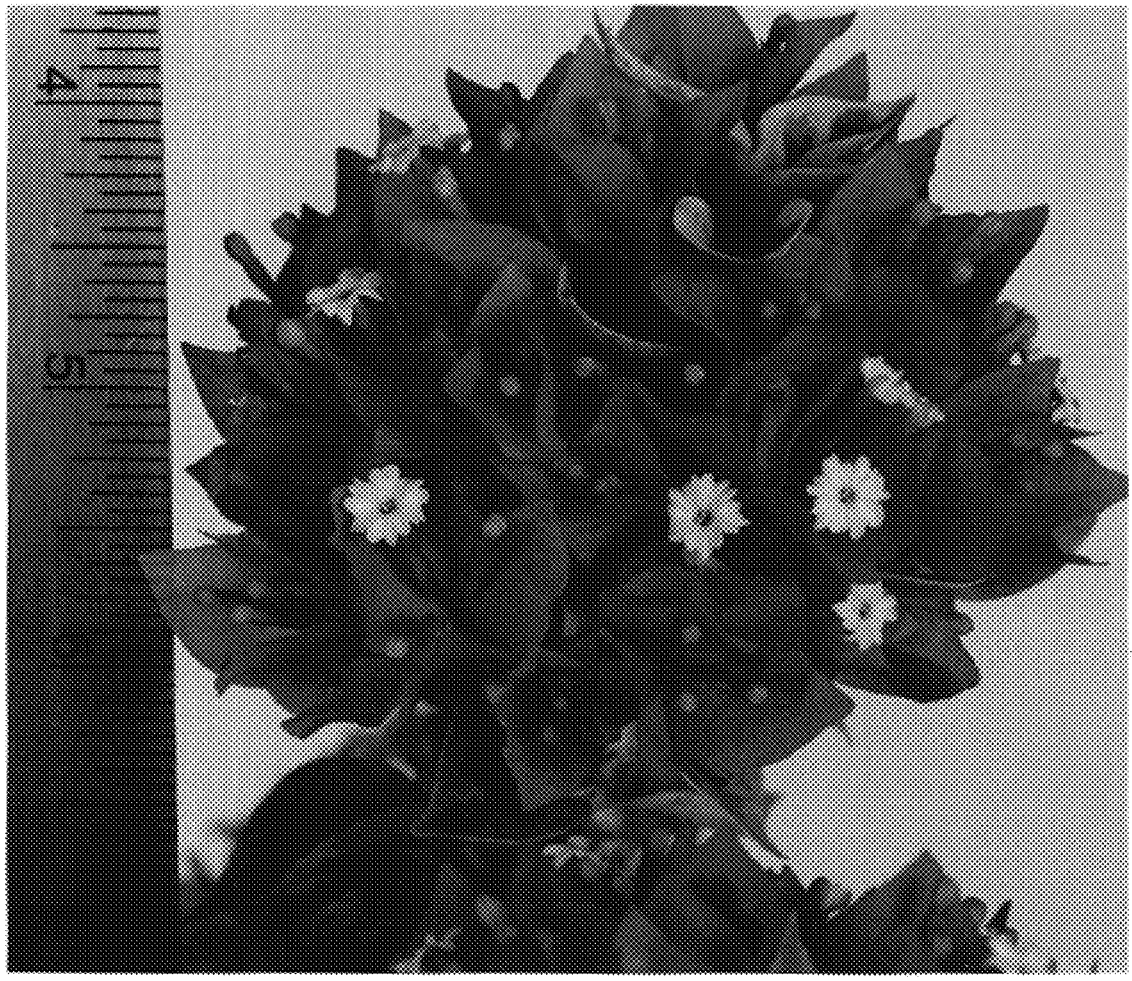
FIGS. 4 and 5 show close-up views illustrating typical developing leaves, flowers and bracts of 'Liberty Flame'.
Figure 5:
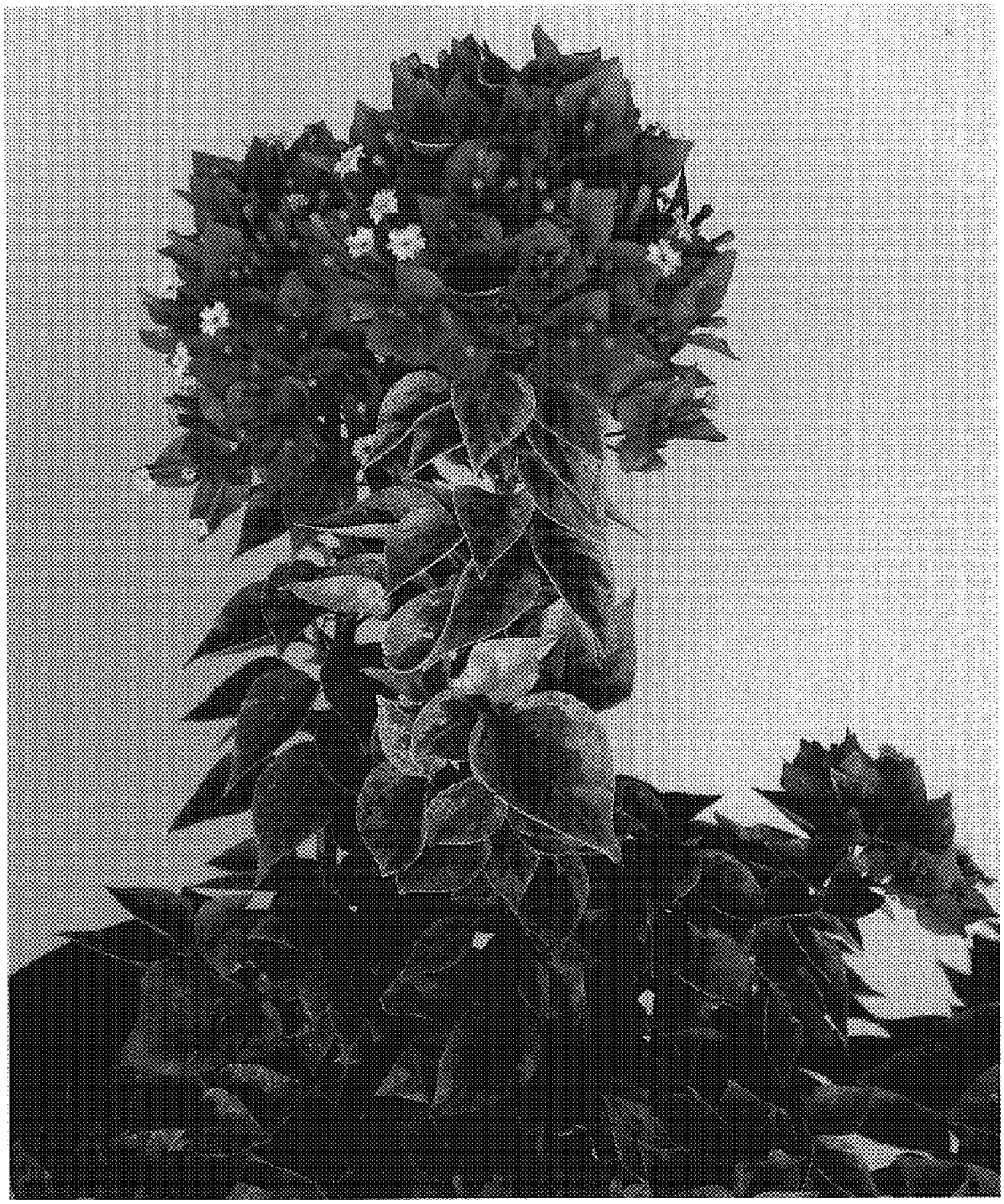
Figure 6:
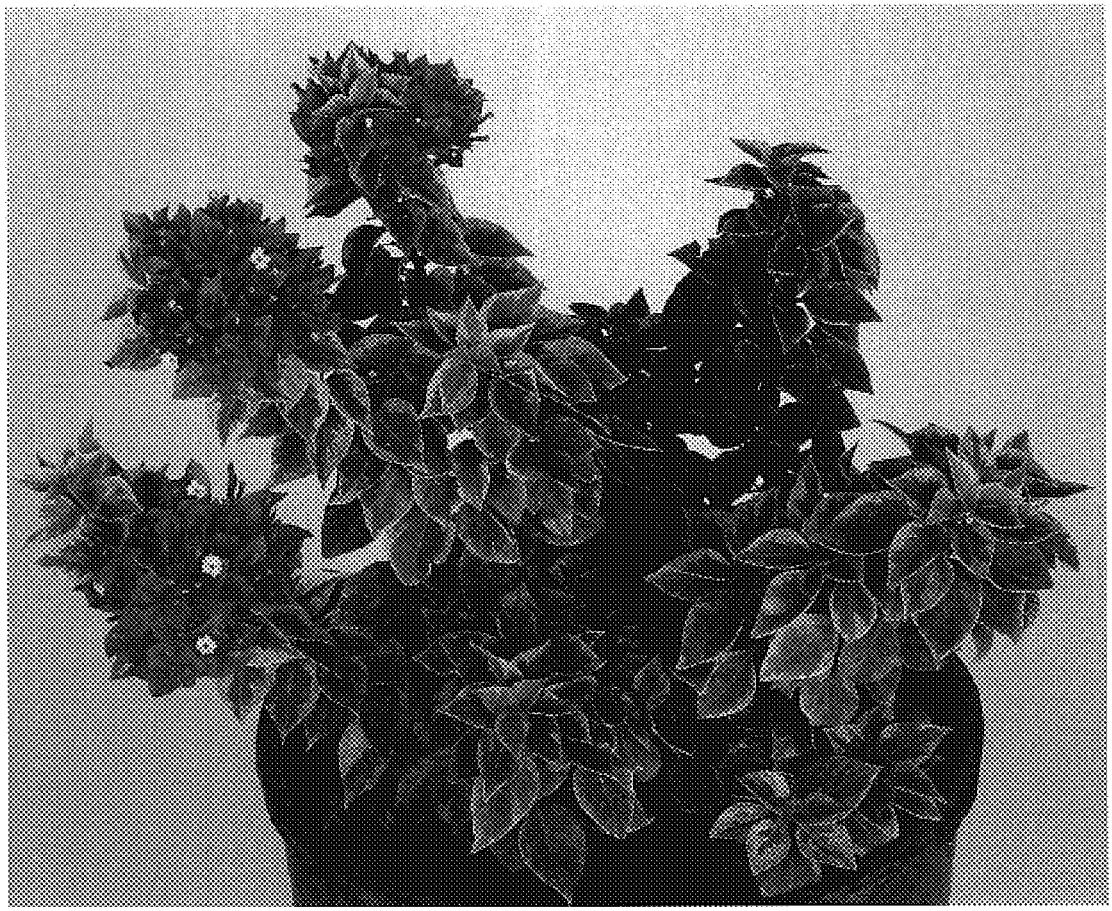
FIG. 6 shows a side perspective view illustrating the variation of leaf variegation.

The following is a detailed description of the new *Bougainvillea* cultivar based upon observation of the plants grown in an outdoor nursery in Cave Creek, Ariz. The color designations stated herein have been determined by a comparison of samples of the new *Bougainvillea* cultivar to the R.H.S. Colour Chart, published by The Royal Horticultural Society of London, England, 1995 Edition. The color references used herein refer to such Chart, except where general terms of ordinary dictionary significance are used. The following observations were made from approximately 6 month-old plants grown outdoors at daytime temperatures ranging from 7° C. to 38° C., nighttime low temperatures of about 0° C., and grown in 25.4 cm containers of 5 gallon capacity.

Botanical classification: *Bougainvillea* libertatis CULTIVAR 'LIBERTY FLAME'.

Origin and parentage: Naturally-occurring branch mutation of *Bougainvillea* 'Torch Glow', U.S. Plant Pat. No. 6,349.

Locality where grown and observed: Cave Creek, Ariz.

Propagation:

*Type.*—Terminal cuttings.

*Time to rooting.*—Seven to ten days during summer months.

*Rooting habit.*—Fibrous and freely branching.

Plant description:

*Appearance.*—Upright to spreading woody growth habit; branches grow to about a half meter.

*Plant height.*—About a half meter from soil level to top of plant plane.

*Plant width/spread.*—About a half meter.

*Growth rate.*—About moderate to rapid.

*Stem description.*—Diameter ranges from about ¼ centimeter to about ½ centimeter. Internode length ranges from about ⅛ centimeter to about 1 centimeter. Color: Young branches are purplish-green and minutely puberulent. As branches mature they turn reddish-brown (ranging from greyed brown 199A to greyed orange 177C and finally medium-gray-brown (greyed green 197D with striations of grey orange 177A) Plant produces a stout, conical thorn, nearly 1 cm long, in axil of each leaf above the node. The mature thorn appears similar in color to the mature bark while the immature thorn resembles the color of the petiole.

Foliage description:

*Arrangement.*—Single, alternate.

*Amount.*—Very Dense.

*Size.*—Largest leaves length: about 3.5 cm. Width: about 2.25 cm.

*Color.*—Variegation is lightest along the margin of the leaf with variable speckling or spotting throughout the entire leaf. Variegation typically becomes darker approaching the center of the leaf. Leaf colors range from yellow-green 144A to yellow-green 146C, and vary less while maturing. Young leaves are variegated on their upper surface with yellow-green 154D along the leaf margin. Mature leaves are variegated with color ranging from about yellow-green 154C to about yellow-green 154B along the leaf margin. The lower surface (of both young and mature foliage) exhibits the same coloration, but is notably less bright and less prominent. The lower surface leaf color is 146C with variegation color of 150D. Venation is lighter than the leaf surface most notably along the midrib where the color appears similar to the petiole.

*Shape.*—Ovate. Apex: Acute. Base: Acute. Margin: Entire.

*Venation.*—Pinnate.

*Texture.*—Smooth upper surface. Lower surface minutely puberulent along midrib.

*Petiole.*—Lighter green than leaf surface, it is yellow green 146C, similar in color to venation. Minutely puberulent. Ranging from 0.5 cm to a little over 1 cm long on a mature leaf.

Flower description:

*Arrangement.*—The floral unit is represented by a three-flowered umbel arranged in axillary cymes with showy and colorful bracts. These cymes are borne in the axils of almost all leaves from near the apex of the branch to five to twenty centimeters down the branch. The inflorescence has three flowers, which are borne on the upper surface of the bract.

*Bracts.*—Bracts subtend each flower, and the pedicel is fused to the midrib of the bract. The upper surface of the bracts is red-purple 60D, with darker venation. The largest bracts are about 2.5 cm long and about 2 cm wide. The shape is ovate, with an acute apex and a rounded base. Venation is pinnate and distinct.

*Peduncle and pedicel.*—The peduncle subtends the bracts and divides into three pedicels. The peduncle and pedicel are greyed purple 187B to 187C and are minutely puberulent. The peduncle averages 0.8 cm in length. The pedicel averages 0.4 cm in length.

*Flower and perianth tube.*—Flower is salver-shaped. The perianth is fused and tubular with the color grayed-orange 176B approximately 1.5 cm in length and the tube 0.25 cm in diameter at its broadest point. The tube is 5 angled and the limb terminates in a five adaxially papillate lobe (approximately 0.5 cm in diameter) with a color of green-white 157B.

*Stamens.*—Not visible, enclosed within calyx, extending almost entirely the length of the perianth. Five to ten. Anthers are yellow.

*Pistil.*—Not visible, enclosed within perianth, extending almost entirely the length of the perianth tube. Single. Lateral with brush like stigma near apex.

Fruits and seeds: Under commercial production conditions to date, the new *Bougainvillea* has not been observed to produce seeds or fruit.

Disease/pest resistance: Under commercial production conditions to date, plants of the new *Bougainvillea* have not been observed to be especially resistant to pathogens or pests common to *Bougainvillea.*

What is claimed is:

1. A new and distinct variety of *Bougainvillea* plant, having the latin name *Bougainvillea libertatis,* and cultivar name 'Liberty Flame', substantially as herein shown and described.

* * * * *